(12) United States Patent
Ling et al.

(10) Patent No.: US 11,071,470 B2
(45) Date of Patent: Jul. 27, 2021

(54) METHOD AND SYSTEM FOR MONITORING A TISSUE PARAMETER SUCH AS PROTEOGLYCAN CONTENT BY MAGNETIC RESONANCE IMAGING

(71) Applicant: UNIVERSITY OF PITTSBURGH—OF THE COMMONWEALTH SYSTEM OF HIGHER EDUCATION, Pittsburgh, PA (US)

(72) Inventors: Wen Ling, Pittsburgh, PA (US); Tao Jin, Pittsburgh, PA (US); Kyongtae Ty Bae, Pittsburgh, PA (US)

(73) Assignee: University of Pittsburgh—Of the Commonvvealth System of Higher Education, Pittsburgh, PA (US)

( * ) Notice: Subject to any disclaimer, the term of this patent is extended or adjusted under 35 U.S.C. 154(b) by 1241 days.

(21) Appl. No.: 15/304,878

(22) PCT Filed: Apr. 22, 2015

(86) PCT No.: PCT/US2015/026976
§ 371 (c)(1),
(2) Date: Oct. 18, 2016

(87) PCT Pub. No.: WO2015/164443
PCT Pub. Date: Oct. 29, 2015

(65) Prior Publication Data
US 2017/0202477 A1 Jul. 20, 2017

Related U.S. Application Data

(60) Provisional application No. 61/982,510, filed on Apr. 22, 2014.

(51) Int. Cl.
*A61B 5/055* (2006.01)
*G01R 33/485* (2006.01)
(Continued)

(52) U.S. Cl.
CPC ............ *A61B 5/055* (2013.01); *A61B 5/4514* (2013.01); *A61B 5/742* (2013.01); *G01R 33/485* (2013.01);
(Continued)

(58) Field of Classification Search
CPC ...................................................... A60B 5/055
See application file for complete search history.

(56) References Cited

U.S. PATENT DOCUMENTS 5,926,023 A * 7/1999 De Groot ........... G01R 33/4641
324/309
6,681,132 B1 1/2004 Katz et al.
(Continued)

*Primary Examiner* — Rochelle D Turchen
(74) *Attorney, Agent, or Firm* — Philip E. Levy; Eckert Seamans Cherin & Mellott, LLC

(57) ABSTRACT

A method of measuring a tissue parameter such as proteoglycan content and other relevant tissue parameters, e.g. tissue pH, in a tissue or an organ of a subject includes generating first and second frequency magnetic resonance data using $T_{1\rho}$ scans at different frequencies, wherein the frequencies are symmetric. The method also includes combining the first frequency magnetic resonance data and the second frequency magnetic resonance data to remove a number of contributions from a number of relaxation mechanisms other than chemical exchange, thereby obtaining chemical exchange-specific magnetic resonance data indicative of the tissue parameter in the tissue or the organ. The chemical exchange-specific magnetic resonance data may be used to measure the proteoglycan content in the tissue or organ.

23 Claims, 11 Drawing Sheets

(51) Int. Cl.
  *G01R 33/56* (2006.01)
  *A61B 5/00* (2006.01)
(52) U.S. Cl.
  CPC ........ *G01R 33/5602* (2013.01); *A61B 5/4523* (2013.01); *A61B 5/4533* (2013.01)

(56) References Cited

U.S. PATENT DOCUMENTS

| | | | | |
|---|---|---|---|---|
| 7,560,925 B1* | 7/2009 | Nishimura | ......... | G01R 33/4828 324/307 |
| 2001/0041834 A1 | 11/2001 | Mugler, III et al. | | |
| 2006/0043970 A1* | 3/2006 | Zaharchuk | ........... | G01R 33/563 324/307 |
| 2007/0167727 A1 | 7/2007 | Menezes et al. | | |
| 2008/0258723 A1* | 10/2008 | Abe | ................... | G01R 33/5613 324/307 |
| 2009/0009168 A1* | 1/2009 | Witschey | ......... | G01R 33/56563 324/307 |
| 2009/0273343 A1 | 11/2009 | Borthakur et al. | | |
| 2010/0166278 A1 | 7/2010 | Witschey | | |
| 2013/0166226 A1* | 6/2013 | Lee | ........................ | G01N 23/02 702/30 |
| 2014/0232391 A1* | 8/2014 | Kadayam Viswanathan | ............... | G01N 24/081 324/303 |
| 2014/0288411 A1* | 9/2014 | Shapiro | ............... | A61K 49/1809 600/420 |
| 2014/0300353 A1* | 10/2014 | He | ..................... | G01R 33/5607 324/309 |
| 2015/0362571 A1* | 12/2015 | Le Fur | ................. | G01R 33/465 324/309 |
| 2016/0081578 A1* | 3/2016 | Gazit | ................... | A61B 5/4824 600/410 |

* cited by examiner

METHOD AND SYSTEM FOR MONITORING A TISSUE PARAMETER SUCH AS PROTEOGLYCAN CONTENT BY MAGNETIC RESONANCE IMAGING

CROSS-REFERENCE TO RELATED APPLICATIONS

This application claims priority under 35 U.S.C. § 119(e) from U.S. provisional patent application No. 61/982,510, entitled "Method and System for Monitoring Proteoglycan Content by Magnetic Resonance Imaging" and filed on Apr. 22, 2014, the contents of which are incorporated herein by reference.

GOVERNMENT CONTRACT

This invention was made with government support under grants #EB003324 and #NS076405 awarded by the National Institutes of Health (NIH). The government has certain rights in the invention.

BACKGROUND OF THE INVENTION

1. Field of the Invention

The present invention pertains to the monitoring and measurement of proteoglycan content in tissues and organs, and in particular, to methods and systems for quantitatively measuring proteoglycan content by magnetic resonance imaging and using the measurements to monitor the onset or progression of connective tissue disorders and diseases. Moreover, the current technique or the further modification or improvement based on current technique can also be able to quantitatively measure other tissue parameters, e.g. pH values, which may be critical to certain pathology such as low back pain.

2. Description of the Related Art

Proteoglycans (PGs) are a major component of the animal extracellular matrix, the "filler" substance existing between cells in an organism. PGs form large complexes, both with other PGs, with hyaluronan and with fibrous matrix proteins (such as collagen). PGs are involved in a wide variety of functions. The function of PGs in connective tissues, e.g. articular cartilage, intervertebral disc, and tendon, is of critical significance. Although all these tissues have slightly different functions, they share some common microscopic structure at the molecular/cellular level. They are made of two major macromolecular components: PG and collagen, featuring, a conglomerate of collagen-formed rigid 3D mesh grids, and flexible PG embedded within the mesh grids. Connective tissues are constantly remodeled by sparsely distributed chondrocytes in response to their micro-environment, e.g. mechanical pressure, pH, etc. The ratio between PG and collagen varies in different tissues: in articular cartilage, PG represents 7% and collagen represents 15% of the total weight; in the intervertebral disc, PG represents 10~15% and collagen represents 15% of the total weight.

Notable diseases with large social and economic impact are associated with connective tissue malfunction, including osteoarthritis (OA), and intervertebral disc degeneration (IDD). IDD is one of the two leading causes of low back pain. Both diseases represent a significant cause of morbidity, with a lifetime incidence of greater than 60%. Despite the high incidence and efforts towards finding an effective therapy, outcomes have not improved and costs for the care of those with OA/low back pain have in fact increased.

Much of the variability and lack of efficacy of current non-operative treatments for connective tissue disorders relates to the difficulty in detecting early macromolecular changes in these tissues. The loss of disc PG is a universal hallmark of the onset of both OA and IDD. Such loss may also have a stronger relationship to active tissue catabolism than loss of collagen due to the relatively short half-life of PG compared with collagen. Moreover, PG matrix destruction occurs much earlier than changes in collagen matrix. As a result, quantitative measurement of PG independent of collagen contribution by magnetic resonance imaging (MRI) is of great value to detect and monitor OA and IDD.

Many biochemical MRI methods have been proposed for assessing physiochemical properties of intervertebral discs/cartilage, specifically PG content. These methods include dGEMRIC (Delayed gadolinium enhanced MRI contrast), $^{23}$Na MRI, gagCEST, $T_2$, and $T_{1\rho}$. The slow diffusion of $Gd(DTPA)^{2-}$ into the spine (3.5 hours) makes dGEMRIC inapplicable in clinical practice. $^{23}$Na MRI has the major limitation of extremely low signal-to-noise (SNR), preventing its utility in intervertebral disc imaging. The applicability of gagCEST for PG assessment has been hampered by many practical limitations (See FIGS. 5b and 5c and Table 1 herein).

Limitations of Current Available $T_2/T_{1\rho}$ Methods

Physically, the relaxation $R_i(=1/T_i, i=2, 1\rho)$ in the connective tissue can generally be expressed as:

$$R_i = R_{i,DD} + R_{i,JE} + R_{i,RDC} + R_{i,CE} \quad [1]$$

where $R_{i,DD}$ stands for relaxation contributed by motion-averaged dipolar-dipolar interaction; $R_{i,JE}$ stands for exchange without chemical shift difference ($\Delta\delta=0$), including diffusion, exchange between cellular space and extracellular space; $R_{i,CE}$ stands for contribution by the sites chemically exchanging (CE) with water, such as —OH, —NH ($\Delta\delta\neq0$), $R_{i,RDC}$ stands for motion-unaveraged contribution from dipolar-dipolar interaction, i.e. RDC.

When i=2, 1ρ, $R_{i,DD}$ and $R_{i,JE}$ are ubiquitous relaxation mechanisms in biological systems (base line). $R_{i,CE}$ is important in the disc because the tissue has high concentrations of —OH and —NH, predominantly from PG (100~300 mM). The ubiquitous magic angle effect in the connective tissue indicates that $R_{i,RDC}$ is an important contributor to the total relaxation rate constant $R_i$ (=1$T_i$, generic $R_i$). The source of $R_{i,RDC}$ is solely from collagen. In fact, due to the dominant ratio of collagen in connective tissue, $R_{i,RDC}$ usually dominates generic $R_i$.

One key aspect about relaxation is that currently available clinical methods for $R_2$ or $R_{1\rho}$ measurements can only detect generic $R_2$ or $R_{1\rho}$, and lack the capability to detect CE-specific $R_2$ or $R_{1\rho}$ separately from the generic relaxation rate.

However, selective detection of relaxation rate from specific relaxation mechanisms such as CE or RDC is of great value. It has been demonstrated in the art that the selective detection of relaxation of $R_{2,CE}$ from generic $R_2$ can readily distinguish human OA cartilage from healthy cartilage. It also distinguishes healthy bovine cartilage from biochemically PG-depleted cartilage. The generic $R_2$ value detected by the clinical $T_2$ method, on the contrary, cannot detect diseased tissue. The prior art results clearly demonstrate that PG's CE contribution to relaxation of cartilaginous tissue alone can readily distinguish OA tissue from healthy tissue without the interference of collagen. The prior art technique, however, is inapplicable in a clinical scanner since it requires the prohibitively high RF power of >1000 uT, which is about 200 times higher than FDA guidelines.

For comparison, as shown in FIG. 1, generic $R_{1\rho}/R_2$ relaxation is also measured using a clinical protocol in phantoms, containing 1% collagen and increasing amounts of chondroitin sulfate (CS), a major component of PG. The results show that the generic $R_2/R_{1\rho}$ value is not only non-linear with respect to CS content, but also has a non-zero baseline, which was even present in the phantom without CS. This is because all the terms in eqn[1] indiscriminately contributed to water relaxation in the phantoms. As the result, the base line always interferes with the correlation between generic $R_2/R_{1\rho}$ and PG content.

In short, although relaxation based quantitative methods, including $T_2$, and $T_{1\rho}$, are major candidates proposed to quantitatively monitor PG content, genenric $T_2/T_{1\rho}$ methods without CE selectivity cannot adequately correlate with PG content, because other relaxation mechanism will interfere with such correlation. In brief, the major physical limitation for PG quantification by relaxation based MRI methods is the inability to selectively detect the CE-specific relaxation rate constant among all the relaxation mechanisms. There is NO current relaxation based method which may detect CE-specific relaxation rate constant.

Limitations of gagCEST

The gagCEST (Glycosaminoglycan Chemical Exchange Saturation Transfer) imaging technique is a prior art method that identifies that PG gives rise to distinctive chemical shifts ranging from between 0.5 ppm and 1.5 ppm. Its contrast can be assessed from the difference between magnetization $M(\delta)$ (FIG. 2a) measured at the labile proton frequency $\delta$(chemical shift) and at the reference frequency of $-\delta$, which is usually referred to as the PTR (proton transfer ratio):

$$PTR(\delta) = \frac{M(-\delta) - M(\delta)}{M(\infty)} \quad [2]$$

where $\delta$ the irradiation offset, and is chosen between 0.5 ppm and 1.5 ppm for PG detection; $M(\delta)$ is bulk magnetization after irradiation; $\infty$ is −300 ppm in FIG. 2a.

Although the original gagCEST is a method with great potential, many limitations still exist to impede its clinical application. gagCEST contrast is a function of $T_1$ and $T_2$ of the targeted tissue, which often changes significantly during disease progression. Magnetic transfer asymmetry (MTasym), which usually complicates gagCEST, is not clearly addressed. Moreover, gagCEST usually requires a long saturation pulse, up to several hundred milliseconds, which is problematic for clinical application due to safety concerns.

Thus, there is a need for a method and system for quantitatively measuring PG content in a clinical context by MRI to detect and monitor the onset and progression of connective tissue disorders and to monitor cell viability.

SUMMARY OF THE INVENTION

In one embodiment, a method of measuring a tissue parameter, such as, without limitation, proteoglycan content, in a tissue or an organ of a subject using magnetic resonance imaging is provided. The method includes generating $T_{1\rho}$ scan data from the tissue or the organ using a first frequency and a second frequency that is symmetric to the first frequency, and manipulating the $T_{1\rho}$ scan data to remove steady-state data contributions at at least one the first frequency and the second frequency and generate data indicative of the tissue parameter in the tissue or the organ. In one particular embodiment, the method includes generating first frequency magnetic resonance data including conducting at least one $T_{1\rho}$ scan of the tissue or the organ at the first frequency and removing a steady-state data contribution at the first frequency such that the first frequency magnetic resonance data is free of the steady-state data contribution at the first frequency, and generating second frequency magnetic resonance data including conducting, at least one $T_{1\rho}$ scan of the tissue or the organ at the second frequency and removing a steady-state data contribution at the first frequency such that the second frequency magnetic resonance data is free of the steady-state data contribution at the second frequency, wherein the second frequency is symmetric to the first frequency. The method also includes combining the first frequency magnetic resonance data and the second frequency magnetic resonance data to remove a number of contributions from a number of relaxation mechanisms other than chemical exchange, thereby obtaining chemical exchange-specific magnetic resonance data indicative of the tissue parameter in the tissue or the organ. The chemical exchange-specific magnetic resonance data may then be used to measure the proteoglycan content in the tissue or the organ.

In another embodiment, an MRI system is provided that includes a permanent magnet, a number of gradient coils, an RF coil, and a control system. The control system includes embedded software that implements the method of the disclosed concept.

In still another embodiment, non-transitory computer readable medium storing one or more programs, including instructions, is provided which when executed by a computer, causes the computer to perform the method of the disclosed concept.

DETAILED DESCRIPTION OF EXEMPLARY EMBODIMENTS

Figure 1:
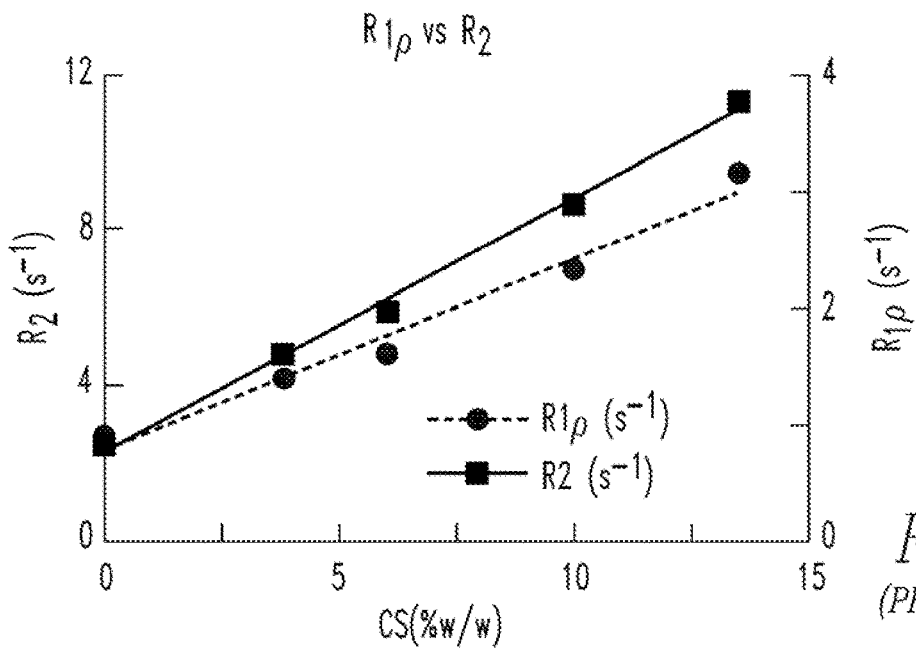
FIG. 1 is a generic $R_{1\rho}/R_2$ relaxation as measured using a clinical protocol.

As used herein, the singular form of "a", "an", and "the" include plural references unless the context clearly dictates otherwise.

As employed herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program and/or a computer. By way of illustration, both an application running on a server and the server can be a component. One or more components can reside within a process and/or thread of execution, and a component can be localized on one computer and for distributed between two or more computers. While certain ways of displaying information to users are shown and described with respect to certain figures or graphs as screenshots, those skilled in the relevant an will recognize that various other alternatives can be employed. The terms "screens," "web page," and "page" are generally used interchangeably herein. The pages or screens are stored and/or transmitted as display descriptions, as graphical user interfaces, or by other methods of depicting information on a screen (whether personal computer, PDA, mobile telephone, or other suitable device, for example) where the layout and information or content to be displayed on the page is stored in memory, database, or another storage facility.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention will now be described, for purposes of explanation, in connection with numerous specific details in order to provide a thorough understanding of the subject invention. It will be evident, however, that the present invention can be practiced without these specific details without departing from the spirit and scope of this innovation.

Figure 3:
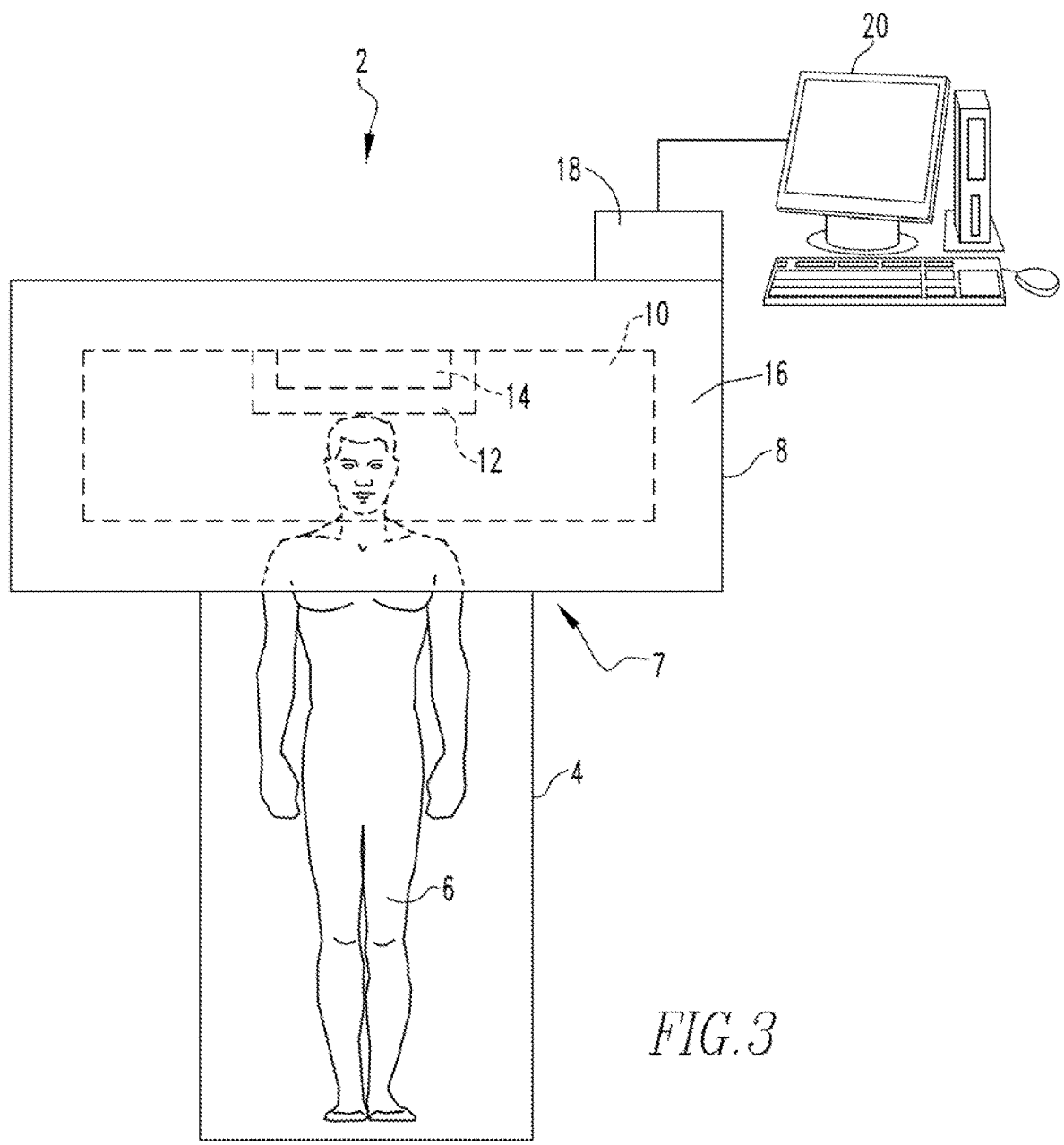
FIG. 3 is a schematic diagram of an exemplary MRI system in which the disclosed concept may be implemented.

The disclosed concept, described in detail herein, provides a method for performing MRI to quantitatively measure PG content in a tissue or organ of a subject. The measurement may be used to detect and monitor the onset and progression of a connective tissue disorder. The concept allows for selective detection of the chemical exchange (CE)-specific relaxation rate constant and thus, for specific detection of PG content in the tissue or organ. The disclosed concept also encompasses a system that performs the disclosed method. One example of such as system is shown in FIG. 3 and described herein. The disclosed method is clinically advantageous because, for example, it does not require use of exogenous agents, specialized MRI hardware or long saturation pulses.

The various particular embodiments of the disclosed concept are described in detail herein. In one exemplary embodiment of the method, four spin-lock $T_{1\rho}$ scans are performed at two symmetric frequencies, +/−Omega, with two scans performed at each frequency. The frequency may be set at +/−(0.6 ppm~2.0 ppm) for PG detection. At each frequency, one spin-lock $T_{1\rho}$ scan and one inverse spin-lock $T_{1\rho}$ scan is conducted. The results from these two scans are combined to remove the steady-state contribution at the specific frequency. The results from the two frequencies are then combined to remove the contribution from relaxation mechanisms other than chemical exchange. In the end, only chemical exchange specific $T_{1\rho}$ is detected, which is specific to PG content in connective tissue. This specific $T_{1\rho}$ may be identified as $R_{1\rho}$,asym.

The concept encompasses various magnetic resonance schemes for performing methods to measure PG content in tissues or organs. For example, in addition to using an irradiation offset Ω between 0.5 ppm and 2.0 ppm, the method encompasses utilizing spin lock (SL) to obtain offset specific $R_{1\rho,Asym}$ contrast at irradiation offset Ω/−Ω. In one embodiment, basic SL and inversion SL may be used. In another embodiment, in addition to applying a 180° pulse to compensate for the $B_1$ inhomogeneity, the inversion pulse may be combined with θ pre-SL pulse. With this combination, the specific absorption rate (SAR) can be reduced. In a further embodiment, the method encompasses compensating for the $B_1$ inhomogeneity by switching SL polarity instead of performing an additional 180° pulse. Additionally, the pre- and post-SL pulse may be replaced with a frequency swept pulse, which may be adiabatic pulses, e.g. adiabatic passage or BIR ($B_1$-insensitive rotation) family. Because the radio frequency amplitude and phase have been varied smoothly between three pulses (they can be combined into one shape pulse), there is no need for $B_1$ inhomogeneity compensation.

Besides conducting SL to obtain $R_{1\rho}$ differentiation as listed above, $R_{1\rho}$ can also be obtained by implementation of adiabatic pulses. For example, by arranging frequency sweep offset (e.g. from +∞ to 0.7 ppm), quantitative measurement of the chemical exchange (CE)-specific relaxation rate constant can be achieved.

FIG. 3 is a schematic diagram of an MRI system 2 according to an exemplary embodiment in which the various embodiments of the glucoCESL methods described herein may be implemented. In particular, the methods described herein, in the various embodiments, may be implemented as a number of software routines embedded in the control system of MRI system 2. Referring to FIG. 3, MRI system 2 includes a table 4 on which a patient 6 rests. Table 4 is structured to slide inside a tunnel 7 formed by a housing 8. Housing 8 houses a superconducting magnet 10, which generates a very high magnetic field. Housing 8 also houses multiple sets of gradient coils 12. Gradient coils 12 are coupled to magnet 10 for adjusting the magnetic field. Housing 8 further houses a Radio Frequency (RF) coil 14, which applies RF pulses to a specific body-part of the patient 6 to be analyzed, and receives signals that are returned by the same body-part. RF coil 6 may be, for example, a surface coil, a saddle coil, a Helmholts coil, or any other suitable RF coil structure. Housing 8 is provided with a magnetic shield 16, which surrounds magnet 10, gradient coil(s) 12 and the RF coil 14. Shield 16 minimizes the magnetic fields generated within tunnel 7 from radiating outside housing 8, and at the same time it protects the inside of tunnel 7 from external magnetic interferences.

MRI system 2 also includes a control module 18 that includes all the components that are required to drive gradient coil 12 and RF coil 14 (for example, an RF transmitter, an output amplifier, and the like); control module 18 also includes all the components that are required to acquire the response signals from the body-part (for example, an input amplifier, an Analog-To-Digital Converter, or ADC, and the like). Moreover, control module 18 drives a motor (not shown) that is used to move the table 342 to and from tunnel 7. Finally, control module 18 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of MRI system 2, including the routines for implementing the various embodiments of the method for quantitatively measuring proteoglycan content described herein.

MRI system 2 further includes a computer system 20 (for example, a Personal Computer, or PC), which is coupled to control module 18. Computer system 20 is configured to control MRI system 2 and to post-process the acquired response signals. Computer system 20 is also configured to display images relating to the body-part under analysis.

As just described, the purpose of the disclosed concept is to provide a clinically applicable MRI method, referred to by the developers as quantitative gagCESL (iGagCESL), which can selectively detect the CE-specific relaxation rate constant, and therefore quantitatively measure PG content in a clinical context. As a consequence, iGagCESL is of great value to detect and monitor the onset and progression of both OA and IDD.

It should be noted that this method does not use any exogenous agents, and remains within clinical guidelines for MR safety. It has clear advantages over both $R_{1\rho}/R_2$ method and gagCEST. Moreover, no specialized MRI hardware, e.g. $^{31}P$ or $^{23}Na$ RF coils, is necessary to conduct the disclosed method, making it easily translatable to the clinic.

The theory behind the iGagCESL of the disclosed concept will now be discussed in detail below. Note the although the disclosed concept is described herein in the exemplary embodiment as being based an SL method due to its simplicity, the disclosed concept can be implemented other techniques such as, without limitation those detailed elsewhere herein.

Recently, the theories of spin-lock (SL) $T_{1\rho}$ technique and CEST method have been unified. Under SL conditions, eqn[1] can be rewritten as:

$$R_{1\rho} = R_{1\rho,misc}(\omega_1) + R_{1\rho,ex}(\delta, \Omega, \omega_1) \quad [3]$$

where $\theta = \arctan(\omega_1/\Omega)$, $\Omega$ is the irradiation offset, $\omega_1$ is the Rabi frequency of the irradiation pulse. This is because CE is the only term of interest here, and all the first three terms in eqn[1] do not contain irradiation offset $\Omega$ or chemical shift $\delta$.

Figure 2A:
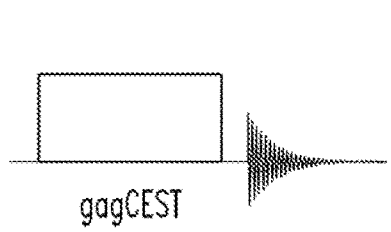
FIG. 2a is a basic pulse diagram showing the prior art gagCEST method.
Figure 2B:
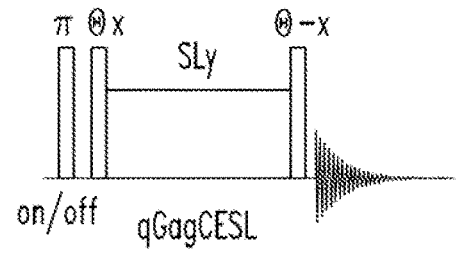
FIG. 2b is a basic pulse diagram showing the qGagCESL method of the disclosed concept.
Figure 2C:
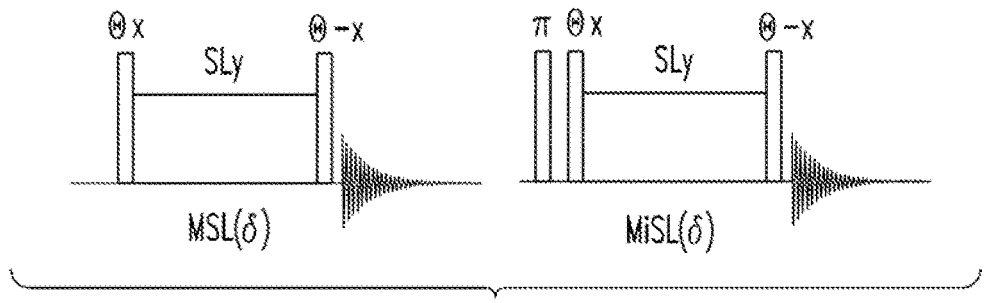
FIG. 2c illustrates the definition of $M_{SL}$ and $M_{ISL}$ according to the disclosed concept.

In general, the normalized bulk magnetization after off-resonance $R_{1\rho}$ at offset $\Omega$ can be expressed as (See FIG. 2c, left):

$$M_{SL}(\Omega) = e^{-R_{1\rho} \cdot TSL} + S_{ss} \cdot (1 - e^{-R_{1\rho} \cdot TSL}) \quad [4]$$

where TSL is SL duration; $M_{SL}(\Omega)$ is bulk magnetization after SL preparation; $S_{ss}$ is steady state of bulk magnetization. Notably, it is the steady state contribution that complicates the effort to extricate $R_{1\rho}$. The steady state should be the same no matter where the magnetization begins. After adding an inversion pulse before SL, the normalized bulk magnetization can be expressed as (See FIG. 2c, right):

$$M_{ISL}(\Omega) = -\alpha \cdot e^{-R_{1\rho} \cdot TSL} + S_{ss} \cdot (1 - e^{-R_{1\rho} \cdot TSL}) \quad [5]$$

where $M_{ISL}(\Omega)$ is bulk magnetization after inversion of SL preparation with inversion efficiency $\alpha$. By subtraction of [5] from [4], and combining with [3], the result is:

$$[M_{SL}(\Omega) - M_{ISL}(\Omega)] = (1+\alpha) \cdot e^{-R_{1\rho} \cdot TSL} = (1+\alpha) \cdot e^{-[R_{1\rho,misc}(\omega_1) + R_{1\rho,ex}(\delta, \Omega, \omega_1)] \cdot TSL} \quad [6]$$

In order to remove $R_{1\rho,misc}(\omega_1)$, $[M_{SL}(-\Omega) \; M_{ISL}(-\Omega)]$ was introduced:

$$[M_{SL}(-\Omega) - M_{ISL}(\Omega)] = (1+\alpha) \cdot e^{-[R_{1\rho,misc}(\omega_1) + R_{1\rho,ex}(\delta, -\Omega, \omega_1)] \cdot TSL} \quad [7]$$

After eqn[6] is divided by eqn[7], the resultant equation can be rearranged as:

$$R_{1\rho,ex}(\delta, \Omega, \omega_1) - R_{1\rho}(\delta, -\Omega, \omega_1) = \frac{1}{TSL} \ln \frac{M_{SL}(-\Omega) - M_{iSL}(-\Omega)}{M_{SL}(\Omega) - M_{iSL}(\Omega)} \quad [8]$$

According to Trott and Palmer's asymmetric population assumption, $$R_{1\rho,ex}(\delta, \Omega, \omega_1) = \frac{p_a \cdot p_b \cdot \delta^2 \cdot k}{(\delta - \Omega)^2 + \omega_1^2 + k^2} \cdot \frac{\omega_1^2}{\Omega^2 + \omega_1^2} \quad [9]$$

where $p_a$ and $p_b$ are relative proton population of water and labile proton ($p_a + p_b = 1$); $\delta$ is chemical shift of labile proton; k is CE rate of labile proton; $\theta$, $\Omega$, and $\omega_1$ are the same as eqn[3].

Set $\Omega$ as $\delta$, which is chemical shift of labile proton of PG between 0.5 ppm and 1.5 ppm, and by combining with eqn[9]:

$$R_{1\rho,asym}(\Omega = \delta, \omega_1) \equiv R_{1\rho,ex}(\delta, \Omega = \delta, \omega_1) - R_{1\rho}(-\delta, \Omega = -\delta, \omega_1)$$
$$= p_a \cdot p_b \cdot k \cdot \frac{1}{1 + \frac{k^2}{\omega_1^2}} \cdot \frac{1}{1 + \frac{w_1^2}{\delta^2}} \cdot \frac{1}{1 + \frac{\omega_1^2 + k^2}{4\delta^2}} \quad [10]$$

Eqn[10] is one of the major outcomes of the disclosed method, and it provides a genuine CE-specific relaxation rate $R_{1\rho,Asym}$, whose analytical form contains only CE parameters ($p_a$, $p_b$, k, $\delta$) and RF parameters ($\Omega$, $\omega_1$). Moreover, Eqn[8] also demonstrates how to measure $R_{1\rho,Asym}$ experimentally.

In brief, eqn[8] and eqn[10] above demonstrate that qGagCESL as shown in eqn[8] should provide a clean and simple approach to detect CE specific relaxation rate constant $R_{1\rho,Asym}$, which is linearly proportional to $p_b$ ($p_a$ is usually water).

Figure 9:
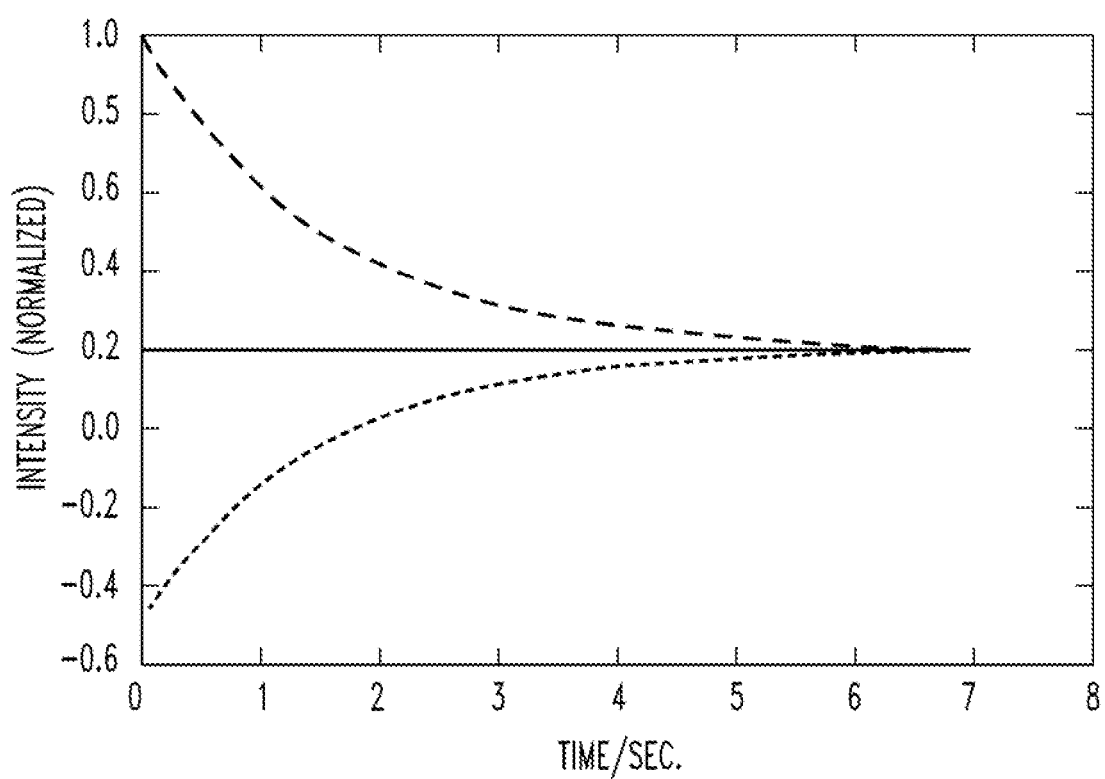
FIG. 9 demonstrates a curve-fitting method that may be employed in connection with the disclosed concept.

In the above paragraphs, the steps in eqn [6] or eqn[7] on each offset of interest, $\Omega$, can also be achieved by a curve-fitting method as shown in FIG. 9, wherein the eqn[4] is demonstrated in the top curve, the eqn[5] is demonstrated in the bottom curve, and the middle red line is the steady state Sss. As can be shown, by fitting multiple (e.g., 5) data points each, $R_{1\rho}$ can be obtained directly for the offset of interest $\Omega$. The steps done in Eqn[8] are the same.

From the above paragraphs, it may also be of clinical interest to repeat the same experiment (e.g. 3 to 20 times) with different RF powers. In this way, more delicate information may be extracted based on more complicated physical and pathological models, as long as the scanning time is sustained with clinical affordable time.

Figure 4A:
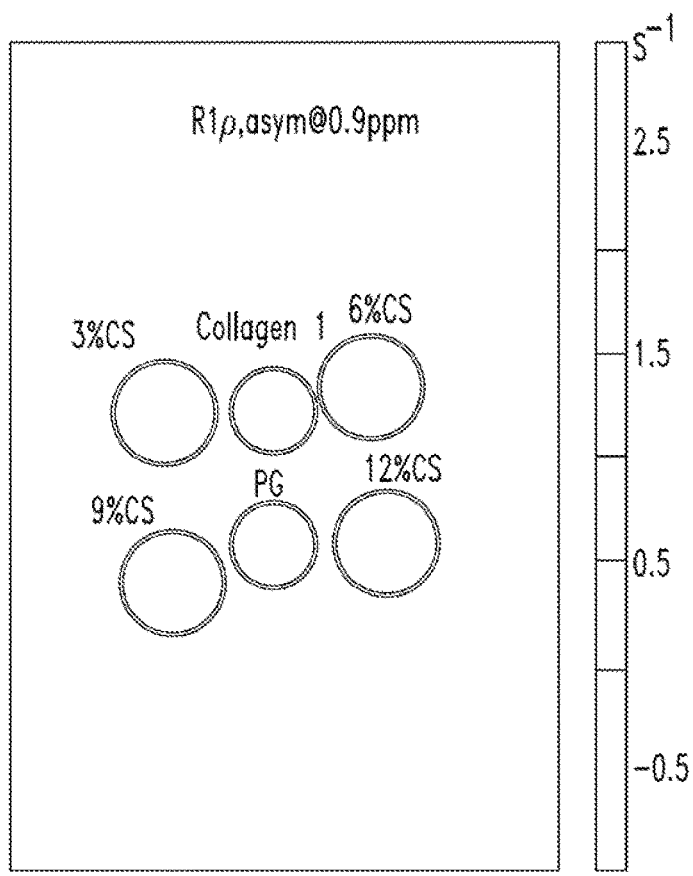
FIGS. 4a and 4b show the contrast produced by the qGagCESL method of the disclosed concept and the prior art gagCEST method.
Figure 4B:
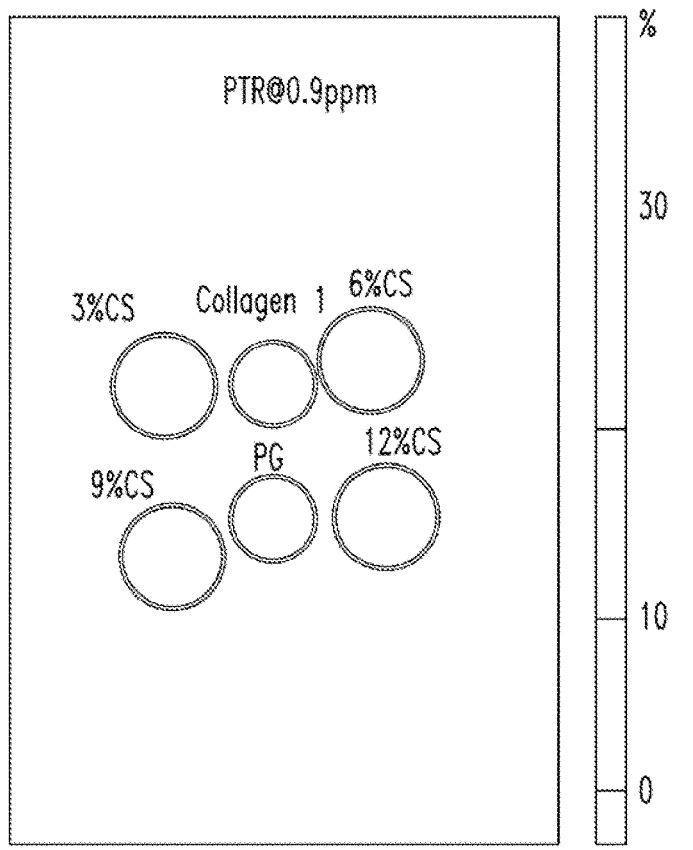
Figure 4C:
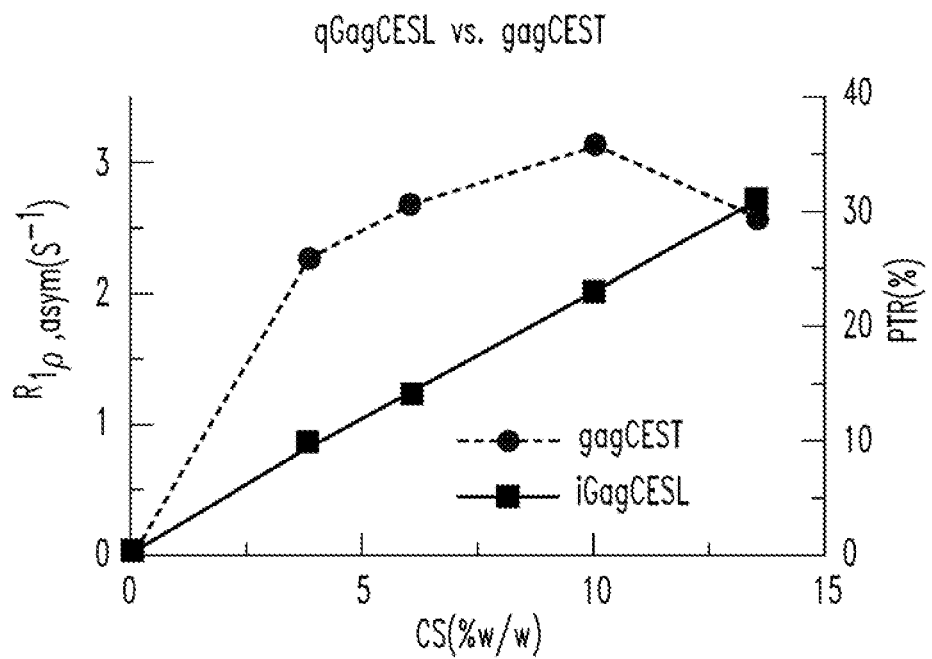
FIG. 4c shows the results of FIGS. 4a and 4b in graphical form.
Figure 4D:
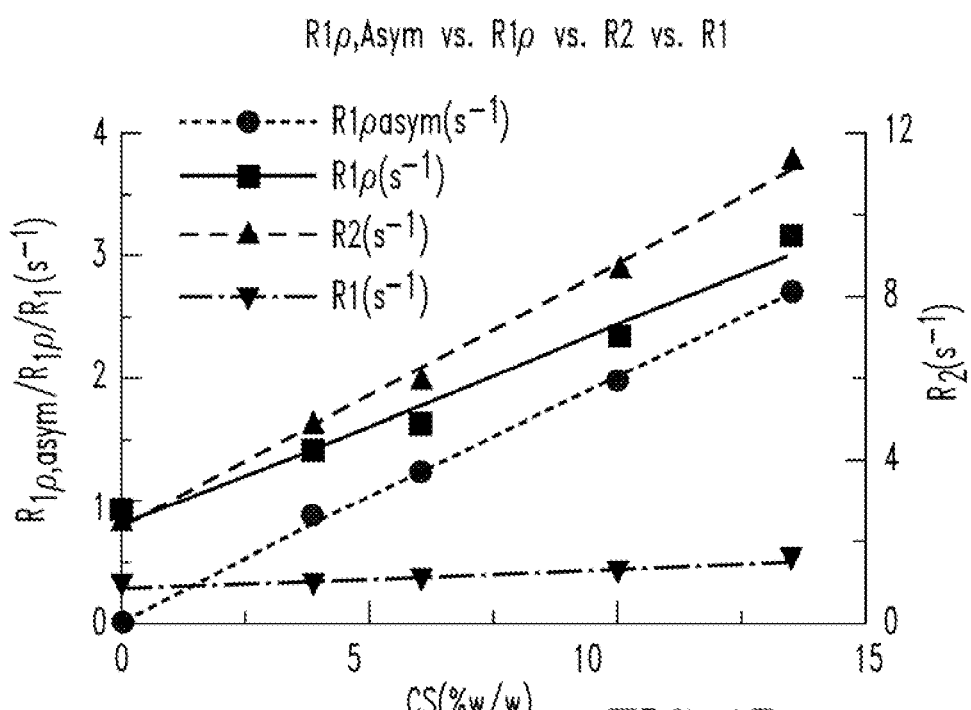
FIG. 4d compares $R_{1\rho,asym}$ of the disclosed concept with $R_{1\rho}$, $R_2$, $R_1$ of the prior art.

The discussion will now turn to preliminary results and a number of advantages of the disclosed concept with reference to FIGS. 4a-4d. FIGS. 4a and 4b show the contrast produced by qGagCESL (FIG. 4a; $R_{1\rho,asym}$, eqn[10], $R_2$=0.9990) and gagCEST (FIG. 4b; PTR, eqn[2]). The results of FIGS. 4a and 4b are summarized in FIG. 4c. In FIG. 4d, $R_{1\rho,asym}$ is compared with $R_{1\rho}$, $R_2$, $R_1$. In FIGS. 4a and 4b, the 0.9 ppm is the irradiation frequency δ in eqn[10] and [2]. For PTR, the normalization frequency is at δ=−300 ppm (the ∞ in eqn[3]). The phantoms contain 1% of collagen I.

As noted above, FIGS. 4a and 4b show a direct visual comparison of qGagCESL(FIG. 4a) and gagCEST (FIG. 4b) in phantoms. The non-linear feature of gagCEST is especially obvious between 9% CS and 12% CS in the PTR map (FIG. 4b). This non-linearity, however, has been completely removed in the $R_{1\rho,asym}$ map (FIG. 4a). The results are summarized in FIG. 4c, which shows that the linear fitting of 5 $R_{1\rho,asym}$ points is almost perfect ($R^2$=0.9990) while PTR yielded non-linear results. FIG. 4c confirms that $R_{1\rho,asym}$ defined in eqn[10] is accurately proportional with $p_a$. Moreover, $R_{1\rho,Asym}$'s selectivity of the CE process is demonstrated by the fact that it vanishes at zero PG content, which is contrary to $R_1$, $R_2$, and $R_{1\rho}$ on the very same phantoms as shown FIG. 4d. This happened only because $R_{1\rho,RDC}$ from the 1% collagen as well as the $R_{1\rho,DD}$ and $R_{1\rho,IE}$ from water in the phantoms have been totally removed. In short, the application of the qGagCESL technique of the disclosed concept allows PG to be measured linearly and quantitatively. In FIGS. 4a-4d, all the results were from a 9.4 T pre-clinical scanner, with RF power of 4.22 uT, which is about ⅓ of the RF deposition of the FDA guidelines.

Figure 5A:
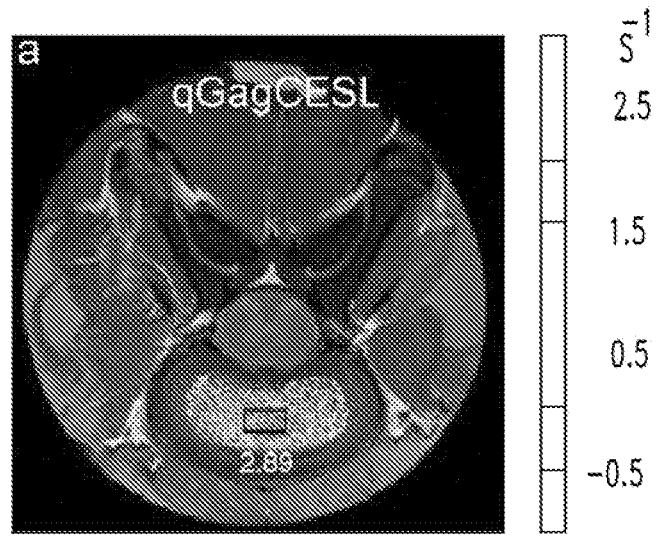
FIGS. 5a-5B illustrate the preliminary work performed by the inventors using rabbit discs.
Figure 5B:
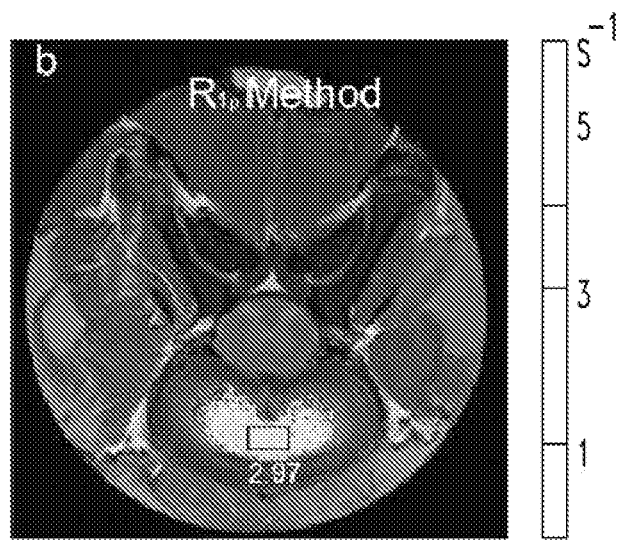

In preliminary work performed by the inventors, a rabbit disc was also scanned with both the qGagCESL method of the disclosed concept and the prior art $R_{1\rho}$ method. Results are shown in FIGS. 5a and 5b, wherein FIG. 5a shows a $R_{1\rho,asym}$ map of the nucleus pulposus in a rabbit disc and FIG. 5b shows a $R_{1\rho}$ map of a nucleus pulposus in a rabbit disc. The numbers are average values in each square region, respectively. The selectivity of qGagCESL over gagCEST is evidenced by the fact that $R_{1\rho,asym}$ at the transitional zone (the edge of nucleus pulposus) is not affected by higher collagen concentration. The nucleus pulposus has a high concentration of PG and low concentration of collagen. The selected square region has very similar values (2.89 s$^{-1}$ vs. 2.97 s$^{-1}$), which indicates that chemical exchange is the primary contributor to $R_{1\rho}$ as the whole in that region. In the region outside the square, the values are different, since $R_{1\rho}$ has a contribution from increased concentration of collagen.

In short, preliminary work performed by the inventors has clearly demonstrated that the qGagCESL method of the disclosed concept can selectively and quantitatively detect PG specific relaxation rate $R_{1\rho,asym}$ without the influence of RDC at clinically applicable RF power, which has never been achieved before.

Figure 6A:
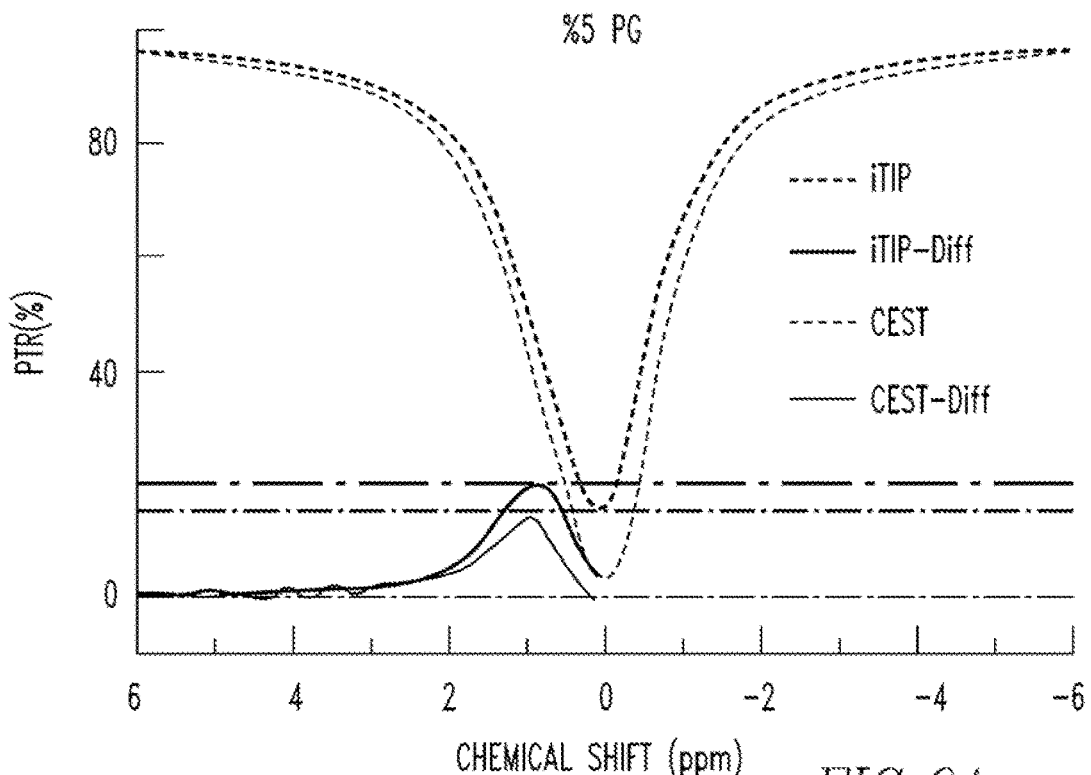
FIGS. 6a-6d illustrate certain advantages of the qGagCESL method of the disclosed concept over the prior art gagCEST method.
Figure 6B:
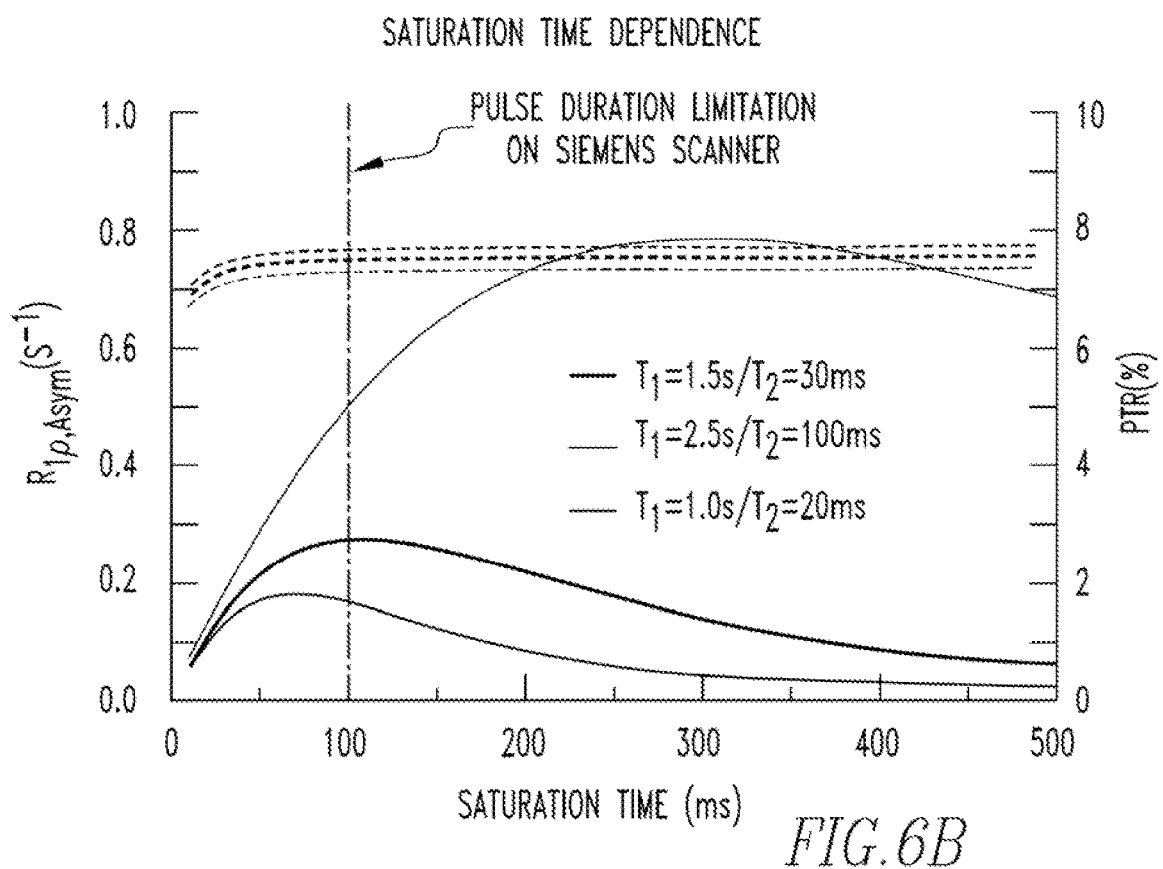
Figure 6C:
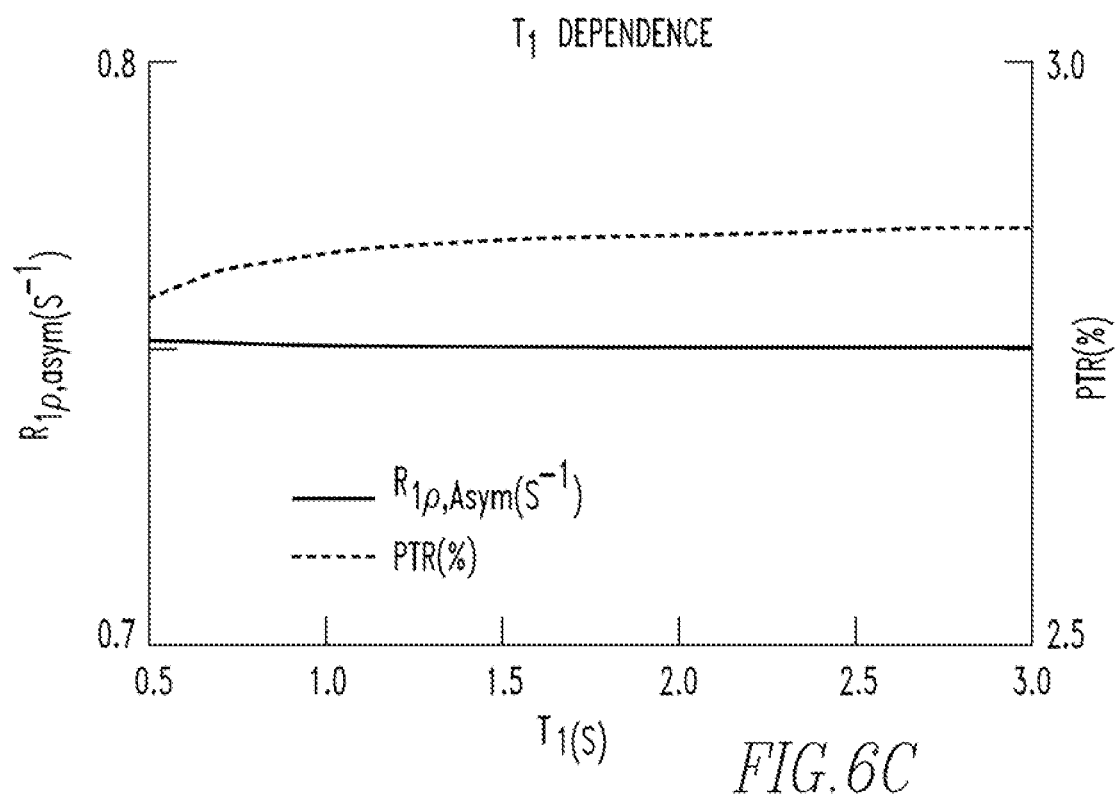
Figure 6D:
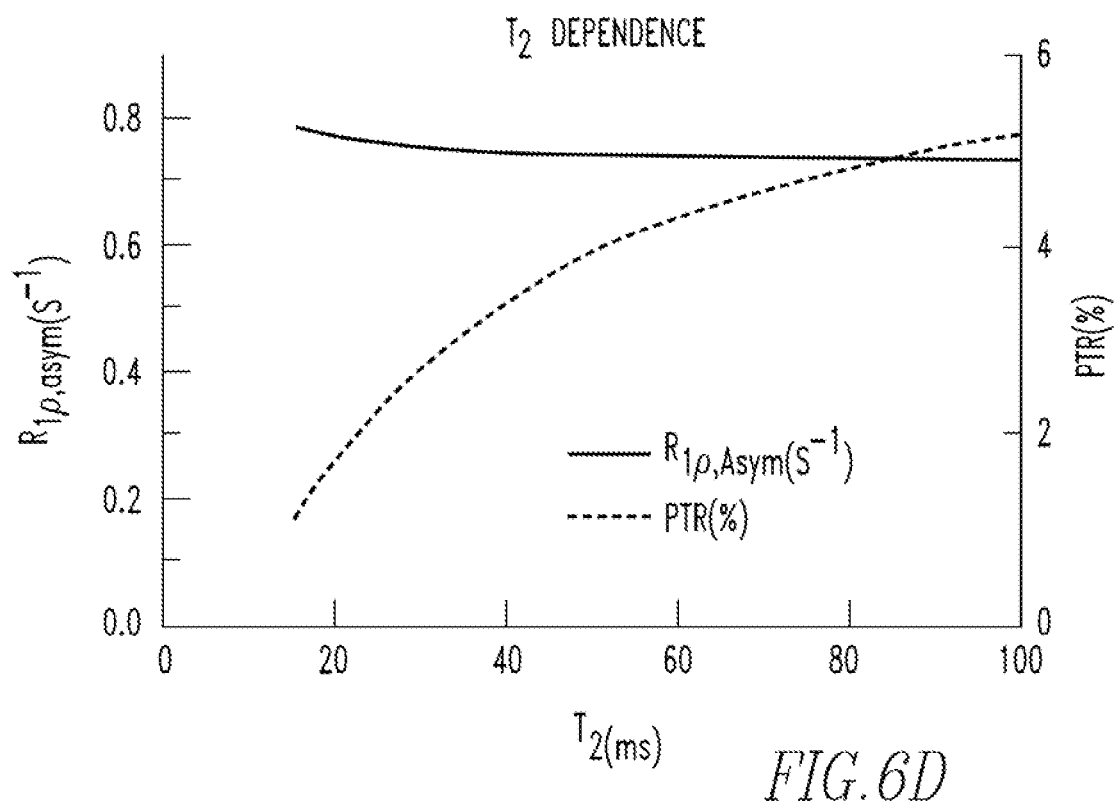

Moreover, there exist several practical limitations for the known gagCEST method, some of which can be well addressed by the iGagCESL method of the disclosed concept. FIG. 6a shows that iGagCESL produces 6.5% higher contrast than gagCEST on PG phantom if the two are expressed as PTR. This increased contrast indicates the better applicability of iGagCESL over gagCEST on a 3T clinical scanner. FIG. 6b shows that $R_{1\rho,asym}$ (broken lines) is constant over saturation pulse length compared to PTR (solid lines), which means that the pulse length limitation in clinical scanner is sufficient (100 ms) for iGagCESL, but insufficient for gagCEST. As shown in FIG. 6b, iGagCESL is preparation tune independent and, as shown in FIG. 6b, iGagCESL is $T_1$ independent. FIG. 6d shows that the variation of T2 has minimal influence on iGagCESL. The insensitivity of $R_{1\rho,asym}$ to $T_1$ and $T_2$ variation as shown in FIGS. 6e and 6d makes quantification robust, since $T_1$ and $T_2$ values vary in different anatomical regions, and maybe at different pathological state.

All the facts listed above demonstrate that iGagCESL is potentially a much more robust method to detect PG content in humans, especially for clinical 3T fields.

In addition, MTasym is one of major complications that faces the gagCEST method. Eqn[2] can be used to evaluate MTasym on a piece of rabbit disc. The preliminary work of the inventors has shown that MTasym is negligible in rabbit discs (−0.33±0.29%). This is very encouraging for the application of iGagCESL since MTasym causes no trouble for PG quantification.

Table 1 below shows other key features of the iGagCESL method of the disclosed concept as compared to the gagCEST, $T_{1\rho}$ methods.

TABLE 1

| | iGagCESL | gagCEST | $T_{1\rho}$ method |
|---|---|---|---|
| Preparation | off-resonance spin-lock at Ω | off-resonance direct saturation at Ω | on/off-resonance spin-lock at Ω |
| Number of offset used | 2 (Ω = −δ, δ) | 3 (Ω = −δ, δ, ∞) | 1 (arbitrary) |
| Irradiation offset | 0.5~2.0 ppm | 0.5~2.0 ppm | arbitrary Ω |
| Irradiation power | 4.0~4.5 μT@0.9 ppm; 1.8~2.2 μT@0.6 ppm; 7.0~7.8 μT@1.2 ppm | 0.5~1.5 μT@1.0 ppm | Usually less than 12 μT |
| Irradiation duration/scheme | Spin-lock duration ≤ 100 ms | Irradiation duration 300~500 ms | Several different spin-lock duration detected |
| Approach to obtain contrast | Eqn[8] | Eqn[2] | Curve-fitting to an exponential decay function |
| Contrast metric | $R_{1\rho,asym}$, in unit s$^{-1}$ | PTR, usually in % | $R_{1\rho}$, in unit s$^{-1}$; $T_{1\rho}$, in unit s |
| $B_0$ distribution/$B_0$ correction | $B_0$ correction is absolutely necessary | $B_0$ correction is absolutely necessary | $B_0$ correction is usually unnecessary |
| $B_1$ distribution | Tolerance to moderate $B_1$ variance. | Accurate $B_1$ distribution is necessary for access PTR | Tolerance to moderate $B_1$ variance. |

Figure 7A:
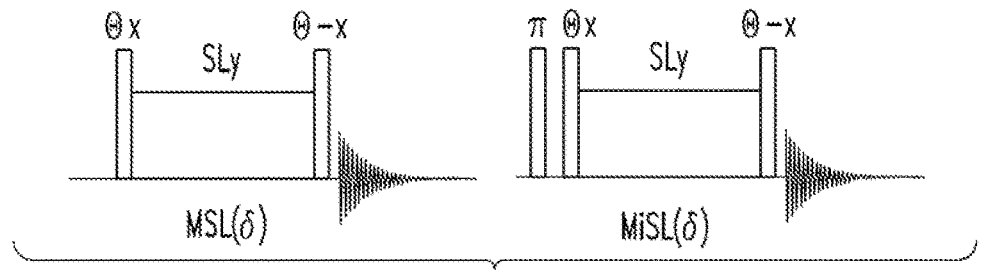
FIGS. 7a-7d show several SL schemes for $R_{1\rho,Asym}$ according to exemplary embodiments of the disclosed concept.
Figure 7B:
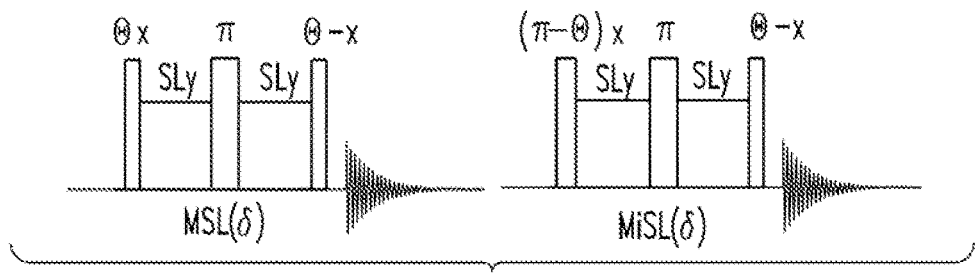
Figure 7C:
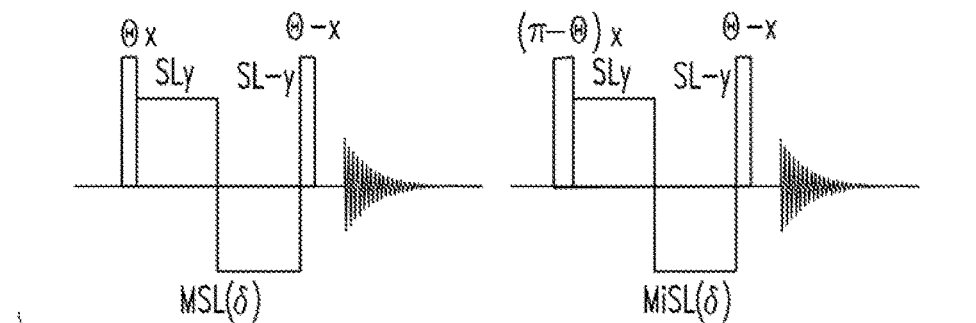
Figure 7D:
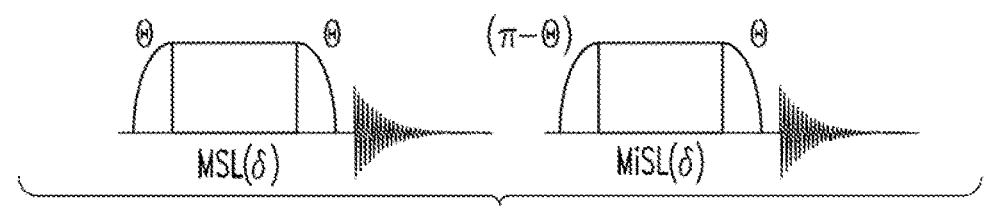

Besides irradiation offset Ω between 0.5 ppm and 1.5 ppm, another distinctive feature of iGagCESL is the ability to utilize SL to obtain offset specific $R_{1\rho,Asym}$ contrast at irradiation offset Ω/−Ω. FIGS. 7a-7d show several SL schemes for $R_{1\rho,Asym}$. FIG. 7a is the basic SL and inversion SL used to demonstrate the idea of iGagCESL. In FIG. 7b, besides applying 180° pulse to compensate for the $B_1$ inhomogeneity, the inversion pulse was combined with θ pre-SL pulse. With this simple combination, specific absorption rate (SAR) can be reduced. The RF in FIG. 7c is different from FIG. 7b in a way that it compensates for the $B_1$ inhomogeneity by switching SL polarity instead of an additional 180° pulse. FIG. 7d replaces the pre- and post-SL pulse of FIG. 7a with frequency swept pulses, which can be adiabatic pulses, e.g. adiabatic passage or BIR ($B_1$-insensitive rotation) family. Since the RF amplitude and phase have been varied smoothly between three pulses (they can be combined into one shape pulse), there is no need for $B_1$ inhomogeneity compensation as in FIGS. 7b and 7c.

Figure 8A:
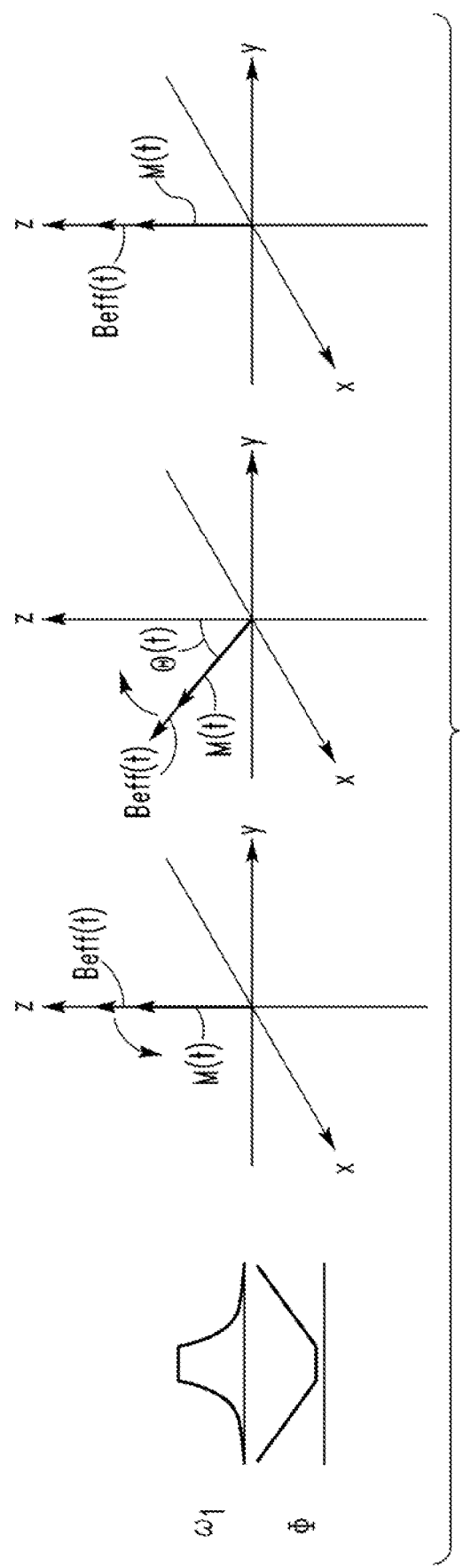
FIGS. 8a and 8b illustrate an exemplary scheme wherein $R_{1\rho}$ can be obtained using the qGagCESL method of the disclosed concept by implementation of adiabatic pulses.
Figure 8B:
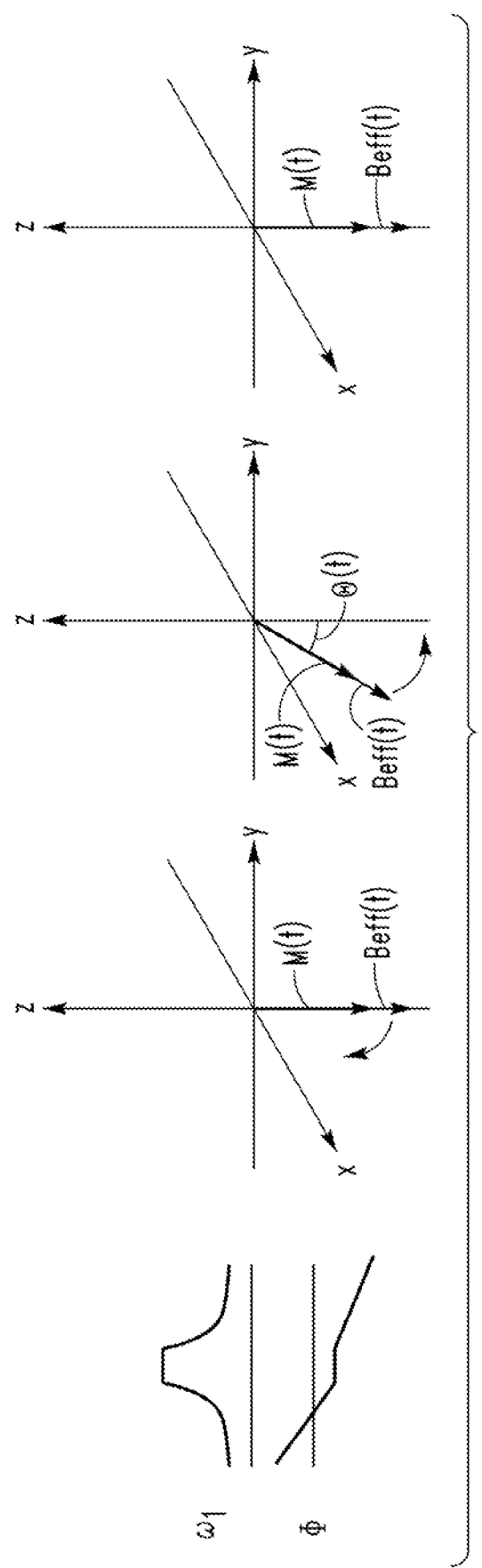

Besides conducting SL to obtain an $R_{1\rho}$ difference as described above, $R_{1\rho}$ can also obtained using iGagCESL by implementation of adiabatic pulses. One possible such scheme is shown in FIGS. 8a and 8b. The illustration shows that adiabatic pulses can also be used to achieve $R_{1\rho}$ detection. By carefully arranging the frequency sweep offset (from +∞ to 0.7 ppm in FIG. 7), iGagCESL can be achieved. FIG. 8a shows the positive SL, process and FIG. 8b shows the negative SL process. Compared to the SL process, which irradiates at fixed offset Ω, the adiabatic process irradiates within a range of offset, e.g. from +∞ to 0.7 ppm in the example shown. Adiabatic implementation of iGagCESL may be advantageous, since PG has several CE sites with different k and chemical offset δ (note here θ(t)≤90°). In the scheme described above, RF is only irradiated at positive Ω. Irradiation at negative Ω can be achieved symmetrically in a rotating frame.

Thus, as described in detail herein, the iGagCESL technique of the disclosed concept provides a method and system for quantitatively measuring PG content in a clinical context by MRI to detect and monitor the onset and progression of connective tissue disorders and to monitor cell viability that has many advantages over prior art methods.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of measuring a tissue parameter in a tissue or an organ of a subject using magnetic resonance imaging, comprising:
    generating $T_{1\rho}$ scan data from the tissue or the organ using a first frequency and a second frequency that is symmetric to the first frequency, wherein the generating the $T_{1\rho}$ scan data includes:
        generating first frequency magnetic resonance data including conducting at least one $T_{1\rho}$ scan of the tissue or the organ at the first frequency and removing a steady-state data contribution at the first frequency such that the first frequency magnetic resonance data is free of the steady-state data contribution at the first frequency, wherein the generating the first frequency magnetic resonance data includes conducting a first spin-lock $T_{1\rho}$ scan of the tissue or the organ at the first frequency to produce first frequency spin-lock data, wherein the first spin-lock $T_{1\rho}$ scan comprises a first spin-lock pulse, conducting a first inverse spin-lock $T_{1\rho}$ scan of the tissue or the organ at the first frequency to produce first frequency inverse spin-lock data, wherein the first inverse spin-lock $T_{1\rho}$ scan comprises a second spin-lock pulse that is an inversion of the first spin-lock pulse, and combining the first frequency spin-lock data and the first frequency inverse spin-lock data to produce the first frequency magnetic resonance data;
        generating second frequency magnetic resonance data including conducting at least one $T_{1\rho}$ scan of the tissue or the organ at the second frequency and removing a steady-state data contribution at the first frequency such that the second frequency magnetic resonance data is free of the steady-state data contribution at the second frequency, wherein the generating the second frequency magnetic resonance data includes conducting a second spin-lock $T_{1\rho}$ scan of the tissue or the organ at the second frequency to produce second frequency spin-lock data, wherein the second spin-lock $T_{1\rho}$ scan comprises a third spin-lock pulse, conducting a second inverse spin-lock $T_{1\rho}$ scan of the tissue or the organ at the second frequency to produce second frequency inverse spin-lock data, wherein the second inverse spin-lock $T_{1\rho}$ scan comprises a fourth spin-lock pulse that is an inversion of the third spin-lock pulse, and combining the second frequency spin-lock data and the second frequency inversion spin-lock data to produce the second frequency magnetic resonance data;
    generating data indicative of the tissue parameter in the tissue or the organ from the first frequency magnetic resonance data and the second frequency magnetic resonance data.

2. The method according to claim 1, wherein the steps of generating first frequency magnetic resonance data and generating second frequency magnetic resonance data further comprise generating data indicative of a first clinical parameter.

3. The method according to claim 1, wherein the tissue parameter is proteoglycan content and the first clinical parameter is PH level of the tissue or organ.

4. The method according to claim 1, further comprising:
    combining the first frequency magnetic resonance data and the second frequency magnetic resonance data to remove a number of contributions from a number of relaxation mechanisms other than chemical exchange, thereby obtaining the data indicative of the tissue parameter in the tissue or the organ comprising chemical exchange-specific magnetic resonance data indicative of the tissue parameter in the tissue or the organ.

5. The method according to claim 4, further comprising using the chemical exchange-specific magnetic resonance data to measure the tissue parameter in the tissue or the organ.

6. The method according to claim 1, wherein the first frequency is between 0.6 ppm and 2.0 ppm.

7. The method according to claim 1, wherein the second frequency is between −2.0 ppm and −0.6 ppm.

8. The method according to claim 1, wherein the first inverse spin-lock $T_{1\rho}$ scan is combined with a first pre-spin-lock pulse and wherein the second inverse spin-lock $T_{1\rho}$ scan is combined with a second pre-spin-lock pulse.

9. The method according to claim 5, wherein the tissue is connective tissue.

10. The method according to claim 1, further comprising using the measured tissue parameter to detect or diagnose a physiological condition in the subject.

11. The method according to claim 1, wherein the combining the first frequency magnetic resonance data and the second frequency magnetic resonance data comprises a division operation, wherein the combining the first frequency spin-lock data and the first frequency inverse spin-lock data comprises a subtraction operation, and wherein the combining the second frequency spin-lock data and the second frequency inverse spin-lock data comprises a subtraction operation.

12. The method according to claim 1, wherein the tissue parameter is proteoglycan content in the tissue or an organ.

13. The method according to claim 1, wherein the generating steps employ one of (i) radiation of 4.0-4.5 μT@0.9 ppm; (ii) 1.8-2.2 μT@0.6 ppm; or (iii) 7.0-7.8 μT@1.2 ppm.

14. The method according to claim 13, wherein the generating steps employ a spin-lock duration of ≤100 ms.

15. An MRI system for use in measuring a tissue parameter in a tissue or an organ of a subject, comprising:
a magnet;
a number of gradient coils;
an RF coil; and
a control system, wherein the control system stores and is structured to execute a number of routines, the number of routines being structured to:
generate $T_{1\rho}$ scan data from the tissue or the organ using a first frequency and a second frequency that is symmetric to the first frequency by:
generating first frequency magnetic resonance data including conducting at least one $T_{1\rho}$ scan of the tissue or the organ at the first frequency and removing a steady-state data contribution at the first frequency such that the first frequency magnetic resonance data is free of the steady-state data contribution at the first frequency, wherein the generating the first frequency magnetic resonance data includes conducting a first spin-lock $T_{1\rho}$ scan of the tissue or the organ at the first frequency to produce first frequency spin-lock data, wherein the first spin-lock $T_{1\rho}$ scan comprises a first spin-lock pulse, conducting a first inverse spin-lock $T_{1\rho}$ scan of the tissue or the organ at the first frequency to produce first frequency inverse spin-lock data, wherein the first inverse spin-lock $T_{1\rho}$ scan comprises a second spin-lock pulse that is an inversion of the first spin-lock pulse, and combining the first frequency spin-lock data and the first frequency inverse spin-lock data to produce the first frequency magnetic resonance data; and
generating second frequency magnetic resonance data including conducting at least one $T_{1\rho}$ scan of the tissue or the organ at the second frequency and removing a steady-state data contribution at the first frequency such that the second frequency magnetic resonance data is free of the steady-state data contribution at the second frequency, wherein the generating the second frequency magnetic resonance data includes conducting a second spin-lock $T_{1\rho}$ scan of the tissue or the organ at the second frequency to produce second frequency spin-lock data, wherein the second spin-lock $T_{1\rho}$ scan comprises a third spin-lock pulse, conducting a second inverse spin-lock $T_{1\rho}$ scan of the tissue or the organ at the second frequency to produce second frequency inverse spin-lock data, wherein the second inverse spin-lock $T_{1\rho}$ scan comprises a fourth spin-lock pulse that is an inversion of the third spin-lock pulse, and combining the second frequency spin-lock data and the second frequency inversion spin-lock data to produce the second frequency magnetic resonance data; and
generate data indicative of the tissue parameter in the tissue or the organ from the first frequency magnetic resonance data and the second frequency magnetic resonance data.

16. The MRI system according to claim 15, number of routines being structured to generate the $T_{1\rho}$ scan data and manipulate the $T_{1\rho}$ scan data by:
combining the first frequency magnetic resonance data and the second frequency magnetic resonance data to remove a number of contributions from a number of relaxation mechanisms other than chemical exchange, thereby obtaining the data indicative of the tissue parameter in the tissue or the organ comprising chemical exchange-specific magnetic resonance data indicative of the tissue parameter in the tissue or the organ.

17. The MRI system according to claim 15, wherein the first frequency is between 0.6 ppm and 2.0 ppm.

18. The MRI system according to claim 15, wherein the second frequency is between −2.0 ppm and −0.6 ppm.

19. The MRI system according to claim 15, wherein the first inverse spin-lock $T_{1\rho}$ scan is combined with a first pre-spin-lock pulse and wherein the second inverse spin-lock $T_{1\rho}$ scan is combined with a second pre-spin-lock pulse.

20. The MRI system according to claim 15, wherein the number of routines are structured to use the chemical exchange-specific magnetic resonance data to measure the tissue parameter in the tissue or the organ.

21. The MRI system according to claim 15, wherein the number of routines are structured to combine the first frequency magnetic resonance data and the second frequency magnetic resonance data using a division operation, to combine the first frequency spin-lock data and the first frequency inverse spin-lock data using a subtraction operation, and to combine the second frequency spin-lock data and the second frequency inverse spin-lock data using a subtraction operation.

22. The MRI system according to claim 15, wherein the tissue parameter is proteoglycan content in the tissue or an organ.

23. A non-transitory computer readable medium storing one or more programs, including instructions, which when executed by a computer, causes the computer to perform the method of claim 1.

* * * * *